United States Patent [19]

Hommann

[11] Patent Number: 4,655,198

[45] Date of Patent: Apr. 7, 1987

[54] HAND-HELD APPLIANCE FOR PERSONAL HYGIENE

[75] Inventor: Edgar Hommann, Grossaffoltern, Switzerland

[73] Assignee: Gimelli & Co AG, Switzerland

[21] Appl. No.: 733,763

[22] Filed: May 14, 1985

[30] Foreign Application Priority Data

May 30, 1984 [DE] Fed. Rep. of Germany ....... 3420213

[51] Int. Cl.$^4$ .............................................. A61H 9/00
[52] U.S. Cl. ....................................... 128/66; 433/80; 251/7
[58] Field of Search ....................... 433/80, 84, 85, 88, 433/95, 100; 251/7, 4; 128/66

[56] References Cited

U.S. PATENT DOCUMENTS

| | | | |
|---|---|---|---|
| 2,825,135 | 3/1958 | Tilden | 433/88 |
| 3,297,558 | 1/1967 | Hillquist | 251/7 |
| 3,496,933 | 2/1970 | Lloyd | 128/66 |
| 4,531,912 | 7/1985 | Schuss et al. | 433/80 |

FOREIGN PATENT DOCUMENTS 0023672 2/1981 European Pat. Off. .............. 433/84

Primary Examiner—John J. Wilson
Attorney, Agent, or Firm—Wegner & Bretschneider

[57] ABSTRACT

A hand-held appliance for mouth and tooth care with a grip portion having a manipulating element that is designed as a sliding switch and that is capable of being shifted in an axial direction. A push button is guided on inclined surfaces in the interior of the shell of the grip portion and reaches through a slot in the shell as well as through a cutout in the manipulating element. In the interior of the grip portion the push button rests on a pinch tube via a ball. The provision of the inclined surfaces results in the push button increasingly moving into the grip portion and increasingly squeezing off a pinch tube when the manipulating element is pushed forward. Independently thereof, the push button is at any given moment capable of being moved into the grip portion far enough to interrupt the water flow.

13 Claims, 5 Drawing Figures

HAND-HELD APPLIANCE FOR PERSONAL HYGIENE

BACKGROUND OF THE INVENTION

This invention relates to a hand-held appliance for personal hygiene, in particular for tooth and mouth care. The appliance is of the type having a grip portion for locating a spray nozzle, the grip portion being provided with an actuating device with a manipulating element for adjusting the flow-rate of a pinch valve provided in the interior of the shell of the hand-held appliance. The hand-held appliance also includes a shut-off device for temporarily interrupting the flow by actuating the same pinch valve without changing the setting of the flow-rate. A hand-held appliance of this kind is for instance described in the prior West German Patent Application No. P 33 47 239.4.

With hand-held appliances of this kind, for instance mouth spray units or oral irrigating appliances used in dentistry, it is essential to be able to set the flow-rate and to temporarily interrupt the flow. This requirement is fulfilled in an oral irrigating appliance used in dentistry, as disclosed in EP-OS No. 0 023 672, which has an actuating ring capable of being turned on a grip portion with the position of the actuating ring governing the extent to which a ball acting as a squeezing element is pressed against a tube to be squeezed off via inclined surfaces. With this appliance the inclined surfaces in the actuating ring are designed in relation to the ball and the other component parts in such a manner that when the actuating ring is in one terminal position, the tube is not squeezed off, and with the actuating ring in another terminal position, it is completely squeezed off.

The hand-held appliance just mentioned has the shortcoming that the actuating ring remains in the position that leads to an interruption of the flow when released. This can result in the pump that delivers the water through the hand-held appliance remaining switched on, without any given necessity, for a prolonged duration of time without being capable of delivering water through the hand-held appliance. For mains-operated mouth spray units the pump motor will be designed in such a manner that the water pressure built up during interrupting the flow through the hand-held appliance is allowed to rise to such an extent that a bypass opens in the pump. In this case the pump produces a noise that is above that present during normal operation. Hence, the user is reminded to switch off the pump. The situation with battery-operated mouth spray units is, however, different in the majority of cases. At least when the battery-operated mouth spray units are set to low water pressure, current keeps flowing through the pump motor when the water flow is interrupted at the hand-held appliance. Hence, it can easily be forgotten to switch off the pump after an interruption of the water flow, resulting in the battery quickly becoming discharged and in the pump motor possibly being damaged or destroyed.

A further shortcoming of the hand-held appliance previously known according to EP-OS No. 0 023 672 rests with the desired flow-rate having to be reset after interrupting the flow. Therefore, the flow-rate setting deemed optimal at one given moment is cancelled with each interruption of the flow.

The shortcoming mentioned last is avoided in the hand-held appliance designed as a mouth-spray unit according to the German Patent Application No. P 33 47 239.4 mentioned at the beginning in that an actuating ring is provided which is capable of being shifted in the longitudinal direction of the grip portion for interrupting the flow and in that the actuating ring is capable of being turned independently thereof for adjusting the flow rate. This provision ensures that the selected flow-rate setting remains unchanged after an interruption of the flow.

The frictional forces that have to be surmounted in order to shift the actuating ring for purposes of interrupting the water flow, are, however, invariably so high that the actuating ring is only capable of automatically returning into a position that allows the water to flow again after an interruption of the flow and after releasing said actuating ring when provision is made of an additional pull-back spring. Such sophistication has, however, become inadequate for most hand-held appliances and automatically renders them susceptible to failure.

SUMMARY OF THE INVENTION

The present invention is based on the primary object of developing a hand-held appliance of the type mentioned at the beginning, with the hand-held appliance constructed such that it is possible to completely interrupt the water flow independently of the flow-rate setting previously selected and automatically returning to the flow-rate setting previously selected the moment the shut-off device provided for interrupting the water flow is released.

This object is established according to the invention in that said shut-off device is a push-button actuating the pinch valve, with said push button being inserted into a cutout in the manipulating element from within the shell. Said push button is capable of being shifted in a slot of the shell, resting against at least one inclined surface of the shell of the grip portion with at least one guiding surface in the interior of the shell, and being capable of being moved along the inclined surface by shifting the manipulating element.

With a hand-held appliance of this kind the push button moves radially into the grip portion as the manipulating element is being shifted, thereby increasingly squeezing off the pinch valve tube provided in the interior of the shell. Independent of the position of the manipulating element the push button can at any given moment be moved farther into the interior of the shell by being depressed, rendering it possible to completely interrupt the flow.

The push-button returns into the position corresponding to that of the manipulating element upon being released, the flow-rate thus being present again as previously set. Given that squeezing of the tube for purposes of interrupting the water flow is effected directly through depression of the push button and not via the inclined control surfaces, the frictional forces to be surmounted are low, the push button thus reliably returning into its starting position upon being released. This provision renders it impossible to permanently interrupt the water flow at the hand-held appliance and to forget to switch off the pump.

Operating the hand-held appliance can be effected with particular ease when the actuating device for adjusting the flow-rate is a sliding switch that is capable of moving axially in relation to the grip portion. It is easier to perform the required shifting movement and the depression of the push button with the thumb of the hand holding the appliance than to shift and turn the actuating ring of the hand-held appliance such as taught by the German Patent Application No. P 33 47 239.4 mentioned at the beginning.

The hand-held appliance is especially simple in its design when at both sides of the pinch valve a guiding surface of the push button makes contact with an inclined surface that is aligned in the axial direction of the grip portion.

Given that the manipulating element with the push button is capable of moving axially and that the pinch valve is, however, stationary, a relative movement between the push button and the pinch valve is brought about when shifting the manipulating element. This relative movement is subject to particularly low friction if the side of the push button facing the pinch valve has an arcuate recess between the guiding surfaces, with the arcuate recess being aligned in the axial direction of the grip portion, and with a ball disposed within, and making contact with, the arcuate recess, the ball in turn resting on the pinch tube and acting as a squeezing element.

A further advantageous embodiment of the invention provides for the sliding switch being capable of being frictionally locked in a plurality of positions by means of notches. The provision of these notches ensures in a simple manner that the sliding switch remains in its respective positions, a flow-rate selected at one given moment thus not being changed unintentionally.

BRIEF DESCRIPTION OF THE DRAWINGS

The invention will be better understood, and objects other than those set forth above, will become apparent, when consideration is given to the following detailed description thereof. Such description makes reference to the annexed drawings wherein.

DETAILED DESCRIPTION OF THE PREFERRED EMBODIMENTS

Figure 1:
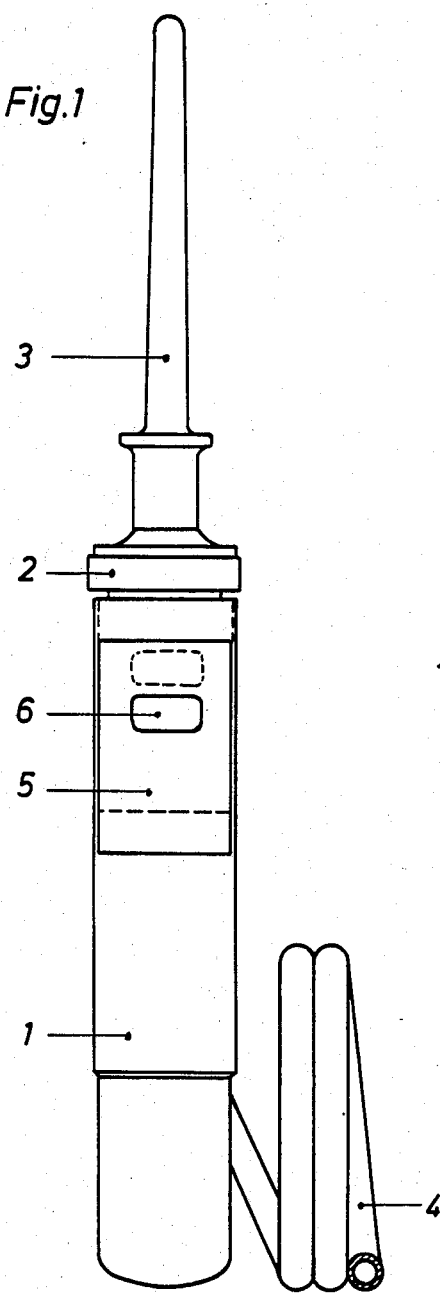
FIG. 1 is a plan view of a hand-held appliance according to the invention.

The hand-held appliance as illustrated in FIG. 1 basically comprises a grip portion 1 with a coupling element 2 into which a spray nozzle 3 is inserted. Water is fed to the grip portion 1 via a tube 4 from a water reservoir not illustrated in the drawing. A manipulating element 5, which is designed as a sliding switch that is capable of being shifted in a longitudinal direction on the grip portion 1, is employed for controlling the flow-rate of the water.

In the manipulating element 5 is a push button 6 which, when depressed, is capable of interrupting the water flow at any given moment and independently of the position of the manipulating element 5.

Figure 2:
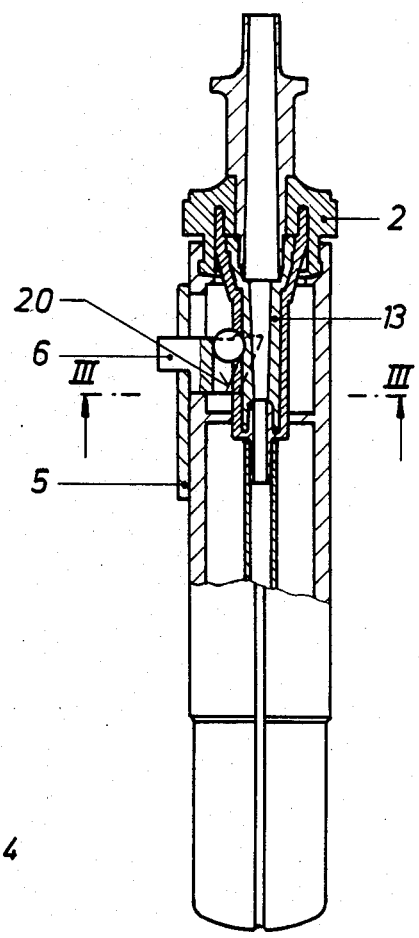
FIG. 2 is a side elevational view, partially in cross-section of the hand-held appliance according to FIG. 1.
Figure 3:
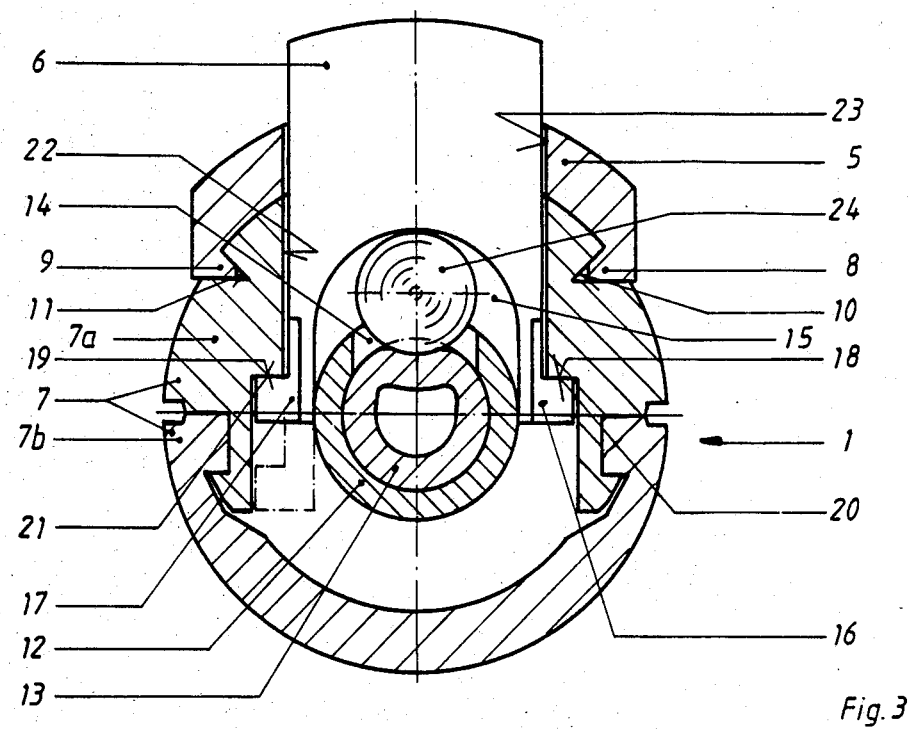
FIG. 3 is a transverse cross-sectional view of the hand-held appliance taken along the line III—III in FIG. 2.

The inner structure of the hand-held appliance is revealed by FIGS. 2 and 3. FIG. 3 shows that the grip portion 1 comprises a shell 7 which consists of two shell halves 7a, 7b, with the latter being connected by snapping into each other. The manipulating element 5 is supported on the outside of the shell half 7a, the movability of said manipulating element 5 being brought about by two guiding projections 8, 9 of the manipulating element 5 each reaching into a guiding groove 10, 11 in the shell half 7a.

In the interior of the grip portion 1 provision is made of a coaxial valve jacket 12 accommodating a pinch tube 13 that feeds the water to the spray nozzle 3. A ball 24 that serves as a squeezing element for squeezing off the pinch tube 13 is arranged in an opening 14 of the valve jacket 12 and rests on the pinch tube 13.

Design and guiding of the push button 6 are essential features of the invention. In the interior of the shell said push button 6 has an arcuate recess 15 with which it rests on the ball 24. On each side of the recess there are guiding projections 16, 17, each of the latter extending outwardly and having stepped guiding surfaces 18, 19 facing upwardly. These guiding surfaces 18, 19 rest against inclined surfaces 20, 21 in the shell half 7a. It is furthermore shown in FIG. 3 that the push button 6 is guided by a slot 22 in the shell half 7a as well as by a cutout 23 in the manipulating element 5 and that said button 6 projects above the manipulating element 5. Due to the elasticity of the pinch tube 13 the ball 24 is biased in an upward direction in the drawing, hence keeping the guiding surfaces 18, 19 of the push button 6 in direct contact with the inclined surfaces 20, 21.

In FIG. 2 an inclined surface 20 is illustrated by a broken line. It can be seen that said inclined surface 20 is directed towards the coupling element 2 and towards the interior of the grip portion 1. As a result, the push button 6 is increasingly moved into the grip portion 1 when the manipulating element 5 is shifted in the direction of the coupling element 2.

Figure 4:
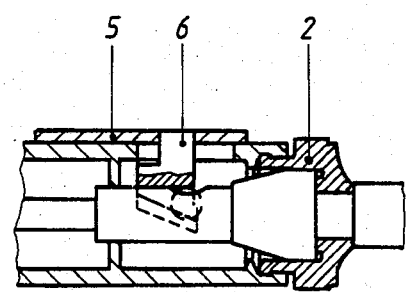
FIG. 4 is a longitudinal cross-sectional view of a center portion of the hand-held appliance showing the manipulating element in a first setting.

FIG. 4 shows the manipulating element 5 in a rearward position and the push button 6 completely depressed, the water flow thereby being interrupted. If released, the push button 6 would move into the position shown in FIG. 2 and would allow the maximum flow rate through the pinch tube 13.

Figure 5:
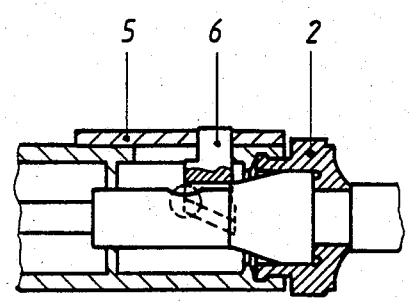
FIG. 5 is a longitudinal cross-sectional view of a center portion of the hand-held appliance showing the manipulating element in a second setting.

In FIG. 5 the manipulating element 5 is shown in its most advanced position in relation to the coupling element 2. Again the push button 6 is completely depressed and interrupts the water flow. If released in this position, only a minor portion of the push button will move out of the manipulating element 5, hence only allowing a small amount of water to flow corresponding to the advanced position of the manipulating element 5.

It should be apparent from the foregoing detailed description, that the objects set forth at the outset to the specification have been successfully achieved. Moreover, while there is shown and described present preferred embodiments of the invention, it is to be distinctly understood that the invention is not limited thereto, but may be otherwise variously embodied and practiced within the scope of the following claims.

What is claimed is:

1. A hand-held appliance for personal hygiene, in particular for tooth and mouth care, comprising a grip portion formed by an essentially hollow shell; a spray nozzle affixed thereto; a pinch valve disposed within said shell for controlling the flow of liquid to said nozzle; an actuating means which comprises a manipulating element for adjusting the flow-rate through said pinch valve, said manipulating element being longitudinally slidingly mounted on the outer surface of said shell; and shut-off means for temporarily interrupting the flow by actuating said pinch valve without changing the setting of the flow-rate; said shut-off means comprising a push button mounted for reciprocal radial movement through an opening in said shell and an opening in said manipulating element, and having two guiding surfaces at a lower portion thereof, each of said guiding surfaces bearing against one of two longitudinal inclined surfaces inside the shell on each side of the pinch valve, said push button being movable along the inclined surfaces by shifting the manipulating element.

2. A hand-held appliance according to claim 1, wherein the manipulating element is a sliding switch that can be shifted axially in relation to the grip portion.

3. A hand-held appliance according to claim 1 or 2, further comprising means to frictionally lock the manipulating element in a plurality of positions.

4. A hand-held appliance for personal hygiene, in particular for tooth and mouth care, comprising a grip portion formed by an essentially hollow shell; a spray nozzle affixed thereto; a pinch valve disposed within said shell for controlling the flow of liquid to said nozzle; an actuating means which comprises a manipulating element for adjusting the flow-rate through said pinch valve, said manipulating element being longitudinally slidingly mounted on the outer surface of said shell; and shut-off means for temporarily interrupting the flow by actuating said pinch valve without changing the setting of the flow-rate; said shut-off means comprising a push button mounted for reciprocal radial movement through an opening in said shell and an opening in said manipulating element, and having at least one guiding surface at a lower portion thereof, said guiding surface bearing against at least one longitudinal inclined surface inside the shell, said push button being movable along the inclined surface by shifting the manipulating element; wherein said push button has an arcuate recess on its bottom surface, with said arcuate recess being aligned in the axial direction of the grip portion, said shut-off means further comprising a ball disposed in said arcuate recess, the ball in turn acting as a squeezing element and resting on the pinch valve.

5. A hand-held appliance according to claim 4, wherein an inclined surface is disposed on each side of said pinch valve aligned in the axial direction of the grip portion with one said guiding surface bearing against each inclined surface.

6. A hand-held appliance according to claim 4, further comprising means to frictionally lock the manipulating element in a plurality of positions.

7. A hand-held appliance according to claim 4, wherein said pinch valve normally biases said push button upwardly, said push button has at least one outwardly extending projection with said guiding surface constituting the top surface of said projection, and said inclined surface is downwardly facing.

8. A hand-held appliance according to claim 4, wherein the manipulating element is a sliding switch that can be shifted axially in relation to the grip portion.

9. A hand-held appliance for personal hygiene, in particular for tooth and mouth care, comprising:
   (a) a grip portion formed by an essentially hollow shell;
   (b) a spray nozzle affixed to one end thereof;
   (c) a pinch valve disposed within said shell for controlling the flow of liquid to said nozzle;
   (d) flow-control means for controlling the flow rate through said pinch valve, comprising a manipulating element which is longitudinally slidingly mounted on the outer surface of the shell; and
   (e) shut-off means for temporarily interrupting the flow through the pinch valve without changing the setting of the flow rate, comprising a radially depressable push button mounted in an opening in the shell and in the manipulating means;
   (f) wherein the inside of said shell has at least one longitudinal inclined surface against which the push button is guided, whereby when the push button is depressed radially, the flow rate is shut off, and when the manipulating element is moved longitudinally, the push button moves along the inclined surface, thereby adjusting the flow rate.

10. A hand-held appliance as claimed in claim 9, wherein the inside of said shell has one longitudinal inclined surface located on each side of the pinch valve for guiding the push button.

11. A hand-held appliance as claimed in claim 9 wherein said push button has an arcuate recess on its bottom surface, said arcuate recess being aligned axially with the grip portion, said shut-off means further comprising a ball disposed in said arcuate recess, the ball resting on the pinch valve and capable of compressing the pinch valve to thereby control the flow rate.

12. A hand-held appliance as claimed in claim 11, wherein the pinch valve normally biases the push button upwardly.

13. A hand-held appliance as claimed in claim 9 further comprising means to frictionally lock the manipulating element in a plurality of positions.

* * * * *